US009492551B2

(12) United States Patent
Bernstein

(10) Patent No.: US 9,492,551 B2
(45) Date of Patent: Nov. 15, 2016

(54) ORALLY ADMINISTRABLE GALLIUM COMPOSITIONS AND METHODS OF USE

(71) Applicant: Lawrence R. Bernstein, Menlo Park, CA (US)

(72) Inventor: Lawrence R. Bernstein, Menlo Park, CA (US)

(*) Notice: Subject to any disclaimer, the term of this patent is extended or adjusted under 35 U.S.C. 154(b) by 0 days.

(21) Appl. No.: 14/457,930

(22) Filed: Aug. 12, 2014

(65) Prior Publication Data
US 2015/0038477 A1 Feb. 5, 2015

Related U.S. Application Data

(63) Continuation of application No. 14/036,576, filed on Sep. 25, 2013, now Pat. No. 9,040,063, which is a continuation of application No. 11/551,815, filed on Oct. 23, 2006, now abandoned.

(60) Provisional application No. 60/730,696, filed on Oct. 27, 2005.

(51) Int. Cl.
| *A61K 47/38* | (2006.01) |
| *A61K 31/555* | (2006.01) |
| *A61K 31/28* | (2006.01) |
| *A61K 31/717* | (2006.01) |
| *A61K 9/00* | (2006.01) |
| *A61K 45/06* | (2006.01) |
| *A61K 33/24* | (2006.01) |
| *A61K 9/20* | (2006.01) |

(52) U.S. Cl.
CPC .............. *A61K 47/38* (2013.01); *A61K 9/0095* (2013.01); *A61K 31/28* (2013.01); *A61K 31/555* (2013.01); *A61K 31/717* (2013.01); *A61K 33/24* (2013.01); *A61K 45/06* (2013.01); *A23K 20/20* (2016.05); *A61K 9/2013* (2013.01); *A61K 9/2054* (2013.01)

(58) Field of Classification Search
None
See application file for complete search history.

(56) References Cited

U.S. PATENT DOCUMENTS

| 3,624,110 A | 11/1971 | Hughes et al. |
| 5,045,565 A | 9/1991 | Gardner et al. |
| 5,258,376 A | 11/1993 | Bernstein |
| 5,525,598 A * | 6/1996 | Collery .................. C07F 5/003 514/187 |
| 5,574,027 A | 11/1996 | Bernstein |
| 5,637,313 A | 6/1997 | Chau et al. |

(Continued)

FOREIGN PATENT DOCUMENTS

| WO | WO-9117751 A1 | 11/1991 |
| WO | WO-0040269 A2 | 7/2000 |

(Continued)

OTHER PUBLICATIONS

Rowe et al., Handbook of Pharmaceutical Excipients, 4th edition, pp. 97-100 (2003).*

(Continued)

*Primary Examiner* — Bethany Barham
*Assistant Examiner* — Barbara Frazier

(57) ABSTRACT

Provided are pharmaceutical gallium compositions that are particularly useful for oral administration. The pharmaceutical compositions include solid, liquid, and paste formulations, which have high oral gallium bioavailability and are suitable for human and veterinary applications. The compositions comprise pharmaceutically acceptable gallium compounds, such as gallium maltolate, gallium 8-quinolinolonate, or gallium nitrate, together with certain viscosity-increasing agents, such as water-soluble forms of methylcellulose or carboxymethylcellulose.

8 Claims, 1 Drawing Sheet

(56) References Cited

U.S. PATENT DOCUMENTS

| | | |
|---|---|---|
| 5,747,482 A | 5/1998 | Bernstein |
| 5,766,622 A | 6/1998 | Nelson |
| 5,883,088 A | 3/1999 | Bernstein |
| 5,900,251 A | 5/1999 | Raissen |
| 5,968,922 A | 10/1999 | Bernstein |
| 5,981,518 A | 11/1999 | Bernstein |
| 5,998,397 A | 12/1999 | Bernstein |
| 6,004,951 A | 12/1999 | Bernstein |
| 6,048,851 A | 4/2000 | Bernstein |
| 6,087,354 A * | 7/2000 | Bernstein ............... A61K 31/28 514/184 |
| 6,261,545 B1 | 7/2001 | Okamoto |
| 2004/0014750 A1 | 1/2004 | Michaelis et al. |
| 2005/0147662 A1 | 7/2005 | Freeman, Jr. |

FOREIGN PATENT DOCUMENTS

| | | |
|---|---|---|
| WO | WO-0124779 A1 | 4/2001 |
| WO | WO-2005058331 | 6/2005 |

OTHER PUBLICATIONS

Jakupec et al., "Gallium in cancer treatment", Current Topics in Medicinal Chemistry, 4(15), pp. 1575-1583 (abstract), 2004.*

Bernstein et al., "Chemistry and Pharmacokinetics of Gallium Maltolate, a Compound with High Oral Gallium Bioavailability," Metal Based Drugs, vol. 7, No. 1, No Month Listed 2000 (pp. 33-47).

Remington, "The Science and Practice of Pharmacy," 2th Edition, Gennaro, ed., No Month Listed 2000 (pp. 1015, 1027, 1028).

* cited by examiner

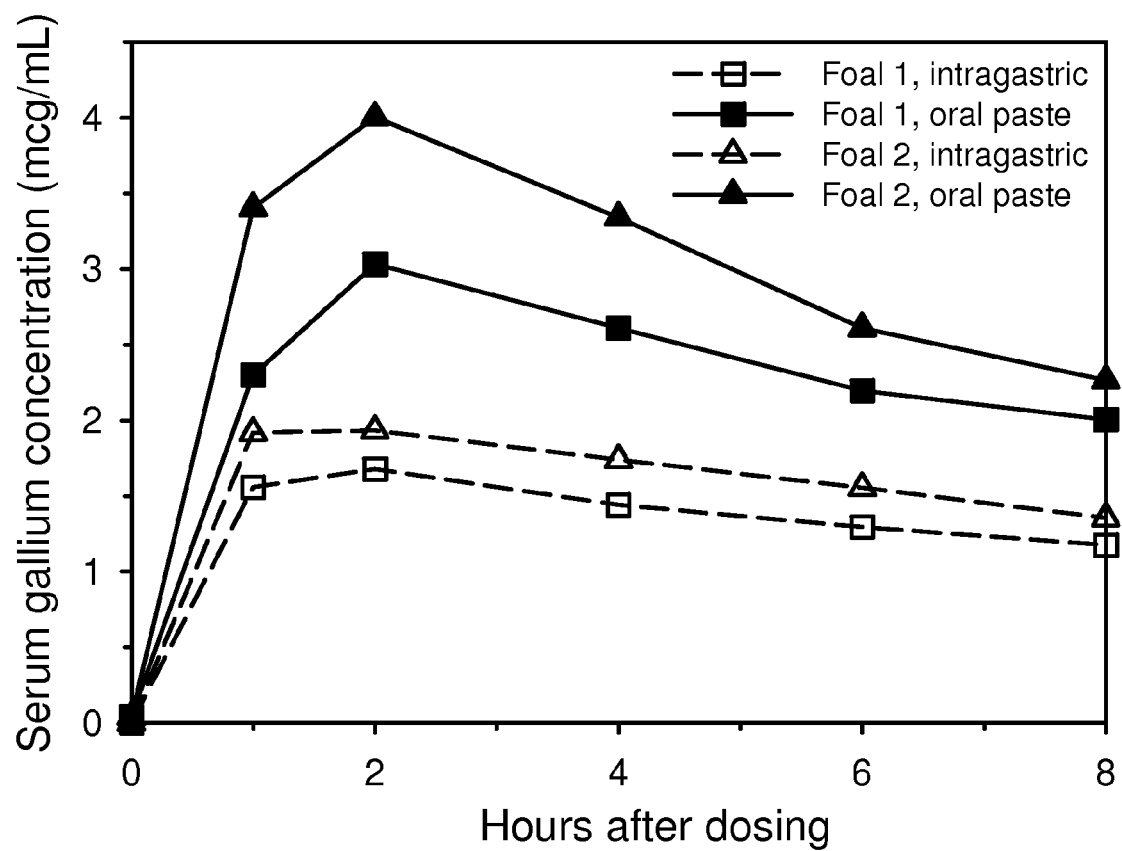

ORALLY ADMINISTRABLE GALLIUM COMPOSITIONS AND METHODS OF USE

CROSS REFERENCE TO RELATED PATENT APPLICATIONS

This application is a continuation of U.S. application Ser. No. 14/036,576 filed on Sep. 25, 2013, which is a continuation of U.S. application Ser. No. 11/551,815, filed Oct. 23, 2006, which claims priority under 35 U.S.C. §119(e) to U.S. Provisional Application No. 60/730,696, filed on Oct. 27, 2005, the disclosure of each application being incorporated by reference herein in its entirety.

TECHNICAL FIELD

This invention relates generally to pharmaceutical compositions comprising gallium. More specifically, this invention relates to the preparation and use of orally administrable gallium pharmaceutical compositions comprising a pharmaceutically acceptable gallium compound, such as for example, gallium maltolate, gallium 8-quinolinolonate, or gallium nitrate, and a viscosity-increasing agent, such as for example, methylcellulose or carboxymethylcellulose.

BACKGROUND OF THE INVENTION

Gallium is used therapeutically and diagnostically in the management and treatment of cancer, infectious disease, inflammatory disease, bone disease, autoimmune disease, and other diseases and disorders. The administration of gallium orally, as compared to administration intravenously or by injection, provides advantages to the patient in terms of convenience, cost, safety, and possibly efficacy.

Most gallium compounds are poorly absorbed when taken orally. A few compounds, including gallium maltolate and gallium 8-quinolinolate, have oral gallium bioavailabilities significantly higher than those of other gallium compounds. Gallium bioavailabilities from these compounds may not, however, always be consistent, and, because the gallium compounds may be acid labile, protection from stomach acid may be needed in some cases.

SUMMARY OF THE INVENTION

With the present invention, the inventor has unexpectedly and surprisingly found that the combination of a pharmaceutically acceptable gallium compound, such as for example, gallium maltolate, with a viscosity-increasing agent, such as for example, methylcellulose or carboxymethylcellulose, can increase the oral bioavailability of gallium.

In a first embodiment of the invention, there is provided a pharmaceutical composition comprising a pharmaceutically acceptable gallium compound and a pharmaceutically acceptable viscosity-increasing agent.

In another embodiment of the invention, there is provided a pharmaceutical composition comprising a pharmaceutically acceptable gallium compound in the solid state, preferably gallium maltolate, mixed with a viscosity-increasing agent, preferably methylcellulose or carboxymethylcellulose, in the solid state.

In a further embodiment of the invention, there is provided a the pharmaceutical composition comprising a drinkable liquid suitable for oral administration (which may be a solution, an emulsion, a gel, a sol, a suspension, or a mixture of these) comprising water with dissolved and/or suspended gallium compound, preferably gallium maltolate, and dissolved and/or suspended viscosity-increasing agent, preferably methylcellulose or carboxymethylcellulose.

In another embodiment of the invention, the pharmaceutical composition of the invention comprises a viscous liquid or paste (which may be a solution, an emulsion, a gel, a sol, a suspension, or a mixture of these) comprising water with dissolved and/or suspended gallium compound, preferably gallium maltolate, and dissolved and/or suspended viscosity-increasing agent, preferably methylcellulose or carboxymethylcellulose.

The solid obtained by evaporation of any of the preceding liquid or partially liquid formulations of the invention is a pharmaceutical composition comprised by an additional embodiment of the invention.

In another embodiment of the invention, the pharmaceutical composition of the invention comprises animal feed to which has been added any of the preceding liquid, partially liquid, viscous liquid, paste, solid, or other formulations of the invention.

In a further embodiment of the invention, there is provided a method of treating or preventing a gallium-responsive disease or disorder in a human or veterinary patient, comprising administering a therapeutically effective amount of the gallium pharmaceutical compositions of the present invention.

In each of the foregoing embodiments, the pharmaceutical composition is preferably adapted for oral administration. In each embodiment, the pharmaceutical compositions may further comprise one or more additional active agents.

The viscosity-increasing agent of each embodiment may be selected from the group consisting of viscosity-increasing forms of methylcellulose, carboxymethylcellulose, hydroxypropyl methylcellulose, and other cellulose derivatives, including their pharmaceutically acceptable salts, esters, hydrates, and solvates, or from the group consisting of viscosity-increasing forms of polyethylene glycol, Carbopols, povidones, gum Arabic, and xanthum gum.

The gallium compound of each embodiment may be selected from the group consisting of gallium nitrate, gallium sulfate, gallium chloride, gallium citrate, gallium acetate, gallium tartrate, gallium gluconate, gallium palmitate, gallium succinate, gallium maltolate, gallium ethyl maltolate, gallium pyridinones, gallium 8-quinolinolate, gallium protoporphyrin IX, gallium pyridoxal isonicotinoyl hydrazone, and bis(2-acetylpyridine 4N-dimethylthiosemicarbazone) gallium(III), gallium(III) tetrachloride.

When the pharmaceutical composition is a solid state mixture of the gallium compound and the viscosity-increasing agent, the weight ratio of the gallium compound to the viscosity-increasing agent is approximately 0.1 to 1000, with a preferred weight ratio of the gallium compound to the viscosity-increasing agent of approximately 1 to 250, and a more preferred weight ratio of the gallium compound to the viscosity-increasing agent of approximately 10 to 100.

When the pharmaceutical composition is a drinkable liquid suitable for oral administration, such as a drinkable solution, an emulsion, a gel, a sol, a suspension, or a mixture of any of the foregoing, the weight ratio of the gallium compound to the viscosity-increasing agent is approximately 0.1 to 1000, with a preferred weight ration of the gallium compound to the viscosity-increasing agent of 1 to 500, and a more preferred weight ratio of the gallium compound to the viscosity-increasing agent of approximately 20 to 200.

When the pharmaceutical composition is a viscous liquid or paste, such as an emulsion, a gel, a sol, a suspension, or a mixture of any of the foregoing, the weight ratio of the gallium compound to the viscosity-increasing agent is approximately 0.1 to 1000, with a preferred weight ratio of the gallium compound to the viscosity-increasing agent of approximately 1 to 500, and a more preferred weight ratio of the gallium compound to the viscosity-increasing agent is approximately 50 to 250. A preferred viscous liquid or paste formulation of the invention comprises 1 to 20% w/v gallium maltolate, 10 to 30% v/v simple syrup, 0.1 to 4% v/v benzyl alcohol, 0.5 to 2.5% w/v carboxymethylcellulose, and a balance of water.

The pharmaceutical composition of each embodiment may further comprise means to prevent or inhibit dissociation of the gallium compound in the acidic environment of the stomach. Such means may be selected from the group consisting of an enteric coating, a buffer, and excess ligand, or means wherein the gallium compound is encapsulated in liposomes.

The pharmaceutical compositions of each embodiment may be in a unit dosage form or in divided or multiple dosage forms.

Additional aspects, advantages and features of the invention will be set forth, in part, in the description that follows, and, in part, will become apparent to those skilled in the art upon examination of the following, or may be learned by practice of the invention.

BRIEF DESCRIPTION OF THE DRAWING

FIG. 1 shows serum gallium concentrations in two foals following the administration to each of 20 mg/Kg gallium maltolate in a single dose, either by intragastric administration of an aqueous formulation without a viscosity-increasing agent, or by oral administration of a viscous liquid/paste formulation containing carboxymethylcellulose.

DETAILED DESCRIPTION OF THE INVENTION

The following definitions are presented to assist one of ordinary skill in the art to which the invention pertains to interpret the description of the invention and the appended claim and are not meant to limit the scope of the invention and appended claims.

As used in the specification and the appended claims, the singular forms "a," "an," and "the" include plural referents unless the context clearly dictates otherwise. Thus, for example, reference to "a viscosity-increasing agent" encompasses a combination or mixture of different viscosity-increasing agents as well as a single viscosity-increasing agent.

The terms "optional" or "optionally" as used herein mean that the subsequently described circumstance may or may not occur, so that the description includes instances where the circumstance occurs and instances where it does not.

The terms "oral administration" and "oral ingestion" refer to all conventional forms for the oral delivery of a pharmaceutical composition and that result in the deposition of the pharmaceutical composition into the gastrointestinal tract (including the gastro portion of the gastrointestinal tract, i.e., the stomach) via the esophagus. Accordingly, oral administration and oral ingestion include, by way of example, actual ingestion of a solid, gel, semisolid, or liquid pharmaceutical composition, oral gavage, nasogastric intubation, and the like.

The term "inhibit dissociation" as used herein means that at least 20%, preferably at least 50%, and more preferably at least 80%, of the complex is not dissociated under acidic conditions (e.g., about pH 2-4) for a period of at least 1 hr and preferably at least 3 hours.

The terms "active agent," "drug," and "pharmacologically active agent" are used interchangeably herein to refer to a chemical material or compound which, when administered to an organism (human or animal, generally human) induces a desired pharmacologic effect.

The terms "to treat" and "treatment" as used herein encompass the usual meanings of these terms plus the usual meanings of the terms "to prevent" and "prevention." Thus, for example, "treatment" of a gallium responsive disease, as the term "treatment" is used herein, encompasses both prevention of a gallium responsive disease in a predisposed individual and treatment of a gallium responsive disease in an individual who has such a disease.

"Viscosity-increasing forms" of compounds are those forms that are water soluble and that increase the viscosity of aqueous solutions in which they are dissolved such that a 1% w/v solution will have a viscosity of at least 10 centipose (cps), and preferably at least 50 cps, and more preferably at least 150 cps, but less than about 30,000 cps, and preferably less than about 10,000 cps. Forms of compounds that are insoluble or nearly insoluble (i.e., solubility less than about 0.01% w/v) in water, such as, for example, cross-linked forms carboxymethylcellulose (e.g., croscarmellose) and povidone (e.g., crospovidone), are not viscosity-increasing agents of this invention.

The term "patient" is meant to include a human or a veterinary patient. Within the context of the present invention, veterinary patients are intended to include both mammalian and non-mammalian veterinary patients, the latter including such veterinary patients as for example, lizards and birds.

Set forth below is a description of what are currently believed to be the preferred embodiments and best examples of the claimed invention. Any alternates or modifications in function, purpose, or structure are intended to be covered by the claims of this application.

As previously noted, the present invention relates to pharmaceutical compositions comprising gallium compounds in combination with certain viscosity-increasing agents. The gallium compositions of the invention have the advantages of retaining high oral gallium bioavailability when exposed to acidic conditions of the stomach, and of retaining high oral gallium bioavailability when administered as a liquid (e.g., Example 6 and FIG. 1).

Pharmaceutically acceptable gallium compounds that may be used to prepare the pharmaceutical compositions of the present invention include, without limitation, inorganic gallium salts, such as gallium nitrate, gallium sulfate, and gallium chloride; organic gallium salts and esters, such as gallium citrate, gallium acetate, gallium tartrate, gallium gluconate, gallium palmitate, and gallium succinate; gallium coordination complexes, including gallium hydroxypyrones, such as gallium maltolate and gallium ethyl maltolate, gallium pyridinones, and gallium 8-quinolinolate; gallium porphyrins, such as gallium protoporphyrin IX (PPIX); gallium pyridoxal isonicotinoyl hydrazone; bis(2-acetylpyridine 4N-dimethylthiosemicarbazone) gallium (III), gallium(III) tetrachloride; and any other pharmaceutically acceptable gallium compounds, salts, organic salts or esters, inorganic compounds, chelates, coordination compounds, and organometallic compounds. Neutral and non-neutral compounds are included, as are salts and esters of the compounds.

Preferred pharmaceutically acceptable gallium compounds from the foregoing list include gallium maltolate, gallium 8-quinolinolate, gallium nitrate, gallium chloride, and gallium sulfate. The more preferred gallium compounds are gallium maltolate, gallium 8-quinolinolate, and gallium nitrate, with gallium maltolate being most preferred. The gallium compound may be neutral or non-neutral.

Viscosity-increasing agents the may be used to prepare the pharmaceutical compositions of the present invention include, without limitation, pharmaceutically acceptable viscosity-increasing forms of, without limitation, methylcellulose, carboxymethylcellulose, hydroxypropyl methylcellulose, and other cellulose derivatives (including their pharmaceutically acceptable salts, esters, hydrates, and solvates), cellulose, polyethylene glycol, Carbopols, povidones, gum Arabic, and xanthum gum, with methylcellulose and carboxymethylcellulose being preferred.

The ability of certain viscosity-increasing agents, in particular methylcellulose or carboxymethylcellulose, to enhance the oral bioavailability of a metal, such as gallium, is unexpected and surprising because cellulose and its derivatives may bind to metals, and might even be expected to form insoluble metal complexes that could decrease oral bioavailability. Without limiting the invention to any particular theory or hypothesis, it is possible that certain viscosity-increasing agents, particularly methylcellulose or carboxymethylcellulose, bind or complex with gallium or a gallium compound in a way that helps protect the gallium or gallium compound from hydrolysis or other degradation in stomach acid. Because these viscosity-increasing agents may also be soluble in the mucus layer of the stomach, further protection from stomach acid may be afforded through transient sequestration in the mucus layer. Once past the stomach, in the duodenum (where most metal absorption is thought to occur), the higher pH and otherwise changed chemical environment allows the gallium or gallium compound to be released and absorbed.

While the viscosity-increasing agents described herein are described within the context of pharmaceutical compositions containing gallium, it is to be understood that the viscosity-increasing agents described herein may be combined with other pharmaceutically acceptable metal compounds to increase the absorption of other metals (such as, for example, iron, cobalt, zinc, copper, indium, manganese, antimony, arsenic, gold, platinum, ruthenium, and lanthanides).

The pharmaceutical compositions of the present invention may be in any acceptable state, such as for example, solid, semisolid, gel, sol, and liquid compositions, as well as mixtures of any of the foregoing. Solid dosage forms include without limitation, tablets, capsules, caplets, lozenges, troches, chewing gums, and beads. Liquid dosage forms include without limitation, liquid solutions, emulsions, suspensions, or combinations thereof. Other dosage forms contemplated under the invention include without limitation, pastes, ointments, creams, aerosols, dusts, shampoos, and powders. Solid or liquid dosage forms wherein the gallium compounds are present in liposomes are also contemplated under the present invention as is animal feed that has been prepared to contain the gallium compositions of the present invention.

While the pharmaceutical compositions of the present invention are preferably formulated in unit dose forms, it is to be understood that they may also be formulated in divided or multiple dose forms.

The pharmaceutical compositions of the invention may comprise one or more pharmaceutically acceptable excipients appropriate to the pharmaceutical form and the intended mode of administration. Such excipients include, without limitation, pharmaceutically acceptable carriers, vehicles, propellants, disintegrants, diluents, dilutants, preservatives, pH adjusters, surface-active substances, emulsifiers, stabilizers, preservatives, coating agents, enteric coatings, buffers, absorption enhancers, solubility modifiers, flavorings, fillers, solvents, gel-forming agents, tablet excipients, antioxidants, dispersants, antifoams, flavor corrigents, solubilizers, colorants, color enhancers, dyes, pigments, permeation promoters, permeation enhancers, complexing agents, absorbents, adsorbents, acidulents, anticaking agents, sequestrants, conditioners, controlled release agents, emollients, emulsifiers, encapsulants, flow aids, fragrances, perfumes, hardeners, stiffeners, humectants, lubricants, moisturizers, odor masking agents, opacifiers, plasticizers solvents, spreading agents, sweeteners, UV absorbers, and viscosity modifiers.

Although the compositions of the invention are designed primarily for oral administration, other modes of administration are possible. Such other modes of administration include, without limitation, topical, transdermal, rectal, buccal, sublingual, vaginal, transurethral, intravenous, intramuscular, intra-arterial, intralesional, topical ocular, intraocular, otic, nasal, and inhaled. For these various modes of administration, the compositions are prepared with suitable vehicles, excipients, carriers, and/or devices (such as patches, implants, and pumps) appropriate to the particular mode of administration, as are well known in the art.

In one embodiment of the invention, a pharmaceutical composition comprises a pharmaceutically acceptable gallium compound in the solid state, preferably gallium maltolate, mixed with a viscosity-increasing agent, preferably methylcellulose or carboxymethylcellulose, in the solid state. Within this embodiment, the weight ratio of the gallium compound to the viscosity-increasing agent is approximately 0.1 to 1000, preferably from approximately 1 to 250, and most preferably from approximately 10 to 100. Examples 1 and 2 describe the preparation of solid state dosage forms of the present invention.

Other pharmaceutically acceptable and chemically compatible components that may be used in the preparation of the solid state dosage forms, including without limitation preservatives, flavorings, colorants, buffering agents, disintegrants, lubricants, binders, coatings (including enteric coatings), and other excipients and active agents. Other pharmaceutically acceptable oral agents that may enhance bioavailability may also be included, such as, for example, carboxylic acids such as citric acid or succinic acid, carboxylates such as sodium citrate or sodium succinate, ascorbic acid, or ascorbates such as sodium ascorbate.

In another embodiment of the invention, the pharmaceutical composition of the invention comprises a drinkable liquid suitable for oral administration (which may be a solution, an emulsion, a gel, a sol, a suspension, or a mixture of these) comprising water with dissolved and/or suspended gallium compound, preferably gallium maltolate, and dissolved and/or suspended viscosity-increasing agent, preferably methylcellulose or carboxymethylcellulose. Within this embodiment, the weight ratio of the gallium compound to the viscosity-increasing agent is approximately 0.01 to 1000, preferably from approximately 1 to 500, and most preferably from approximately 50 to 250. Example 3 describes the preparation of a liquid state dosage form of the present invention.

Other pharmaceutically acceptable and chemically compatible components that may be used in the preparation of the liquid state dosage forms include without limitation preservatives, flavorings, colorants, desensitizing agents, pH-adjusting agents, buffering agents, and other excipients and active agents. Preferred preservatives include benzyl alcohol, ascorbic acid, methyl paraben, butyl paraben, and propyl paraben, with benzyl alcohol being particularly preferred. Optionally, the pH can be adjusted to approximately 6-7.5; preferred pH-adjusting agents include HCl and $Na_2CO_3$. Other pharmaceutically acceptable oral agents that may enhance bioavailability may also be included, such as, for example, carboxylic acids such as citric acid or succinic acid, carboxylates such as sodium citrate or sodium succinate, ascorbic acid, or ascorbates such as sodium ascorbate.

In a further embodiment of the present invention, the pharmaceutical composition of the invention comprises a viscous liquid or paste (which may be a solution, an emulsion, a gel, a sol, a suspension, or a mixture of these) comprising water with dissolved and/or suspended gallium compound, preferably gallium maltolate, and dissolved and/or suspended viscosity-increasing agent, preferably methylcellulose or carboxymethylcellulose. Within this embodiment, the weight ratio of the gallium compound to the viscosity-increasing agent is approximately 0.01 to 1000, preferably from approximately 1 to 500, and most preferably from approximately 20 to 200. Example 4 describes a viscous liquid/paste dosage form of the present invention.

Other pharmaceutically acceptable and chemically compatible components may also be present, including preservatives, flavorings, colorants, desensitizing agents, pH-adjusting agents, and other excipients and active agents. Optionally, the pH can be adjusted to approximately 6-7.5; preferred pH-adjusting agents include HCl and $Na_2CO_3$. Preferred preservatives include benzyl alcohol, ascorbic acid, methyl paraben, butyl paraben, and propyl paraben, with benzyl alcohol being particularly preferred. Other pharmaceutically acceptable oral agents that may enhance bioavailability may also be included, such as, for example, carboxylic acids such as citric acid or succinic acid, carboxylates such as sodium citrate or sodium succinate, ascorbic acid, or ascorbates such as sodium ascorbate.

The viscous liquid or paste dosage forms described above are particularly suitable for oral administration to many mammals, particularly large mammals such as, for example, horses and other equids, bovine animals such as cattle, sheep, goats, cats, and dogs. For this purpose, the viscous liquid or paste may be put into a syringe and squirted into the back of the mouth, or otherwise administered to the mouth, from where it is swallowed.

In yet another embodiment of the present invention, the solid pharmaceutical composition of the present invention is obtained by evaporation of any of the preceding liquid or partially liquid formulations. The solid obtained by evaporation of a liquid comprising gallium maltolate and methylcellulose or carboxymethylcellulose (such as the liquid formulation of Example 3) is a preferred pharmaceutical composition of the invention. Within this embodiment, the weight ratio of the gallium compound to the viscosity-increasing agent is approximately 0.01 to 1000, preferably from approximately 1 to 500, more preferably from approximately 10 to 250, and most preferably from approximately 20 to 200.

Evaporation may be accomplished by drying methods well known in the art (e.g., Remington: The Science and Practice of Pharmacy, 20$^{th}$ Edition, Gennaro, A. R., Ed., Lippincott, Williams and Wilkins, 2000). Such methods include, without limitation, drying at room temperature or at elevated temperatures of up to about 90° C. in air or in a partial vacuum, on exposed trays with or without shaking, in ovens or vacuum ovens, in rotary evaporators, and so on.

In still another embodiment of the present invention, the pharmaceutical composition of the invention comprises animal feed to which has been added any of the preceding liquid, partially liquid, viscous liquid, paste, solid, or other formulations of the invention. Example 5 describes the preparation of animal feed containing the gallium compositions of the present invention.

Any of the pharmaceutical compositions described above may further include means to prevent or inhibit dissociation of the gallium compound in the acidic environment of the stomach. Such means are well known in the art, and are recited in standard pharmaceutical manufacturing textbooks (e.g., Remington: The Science and Practice of Pharmacy, 20$^{th}$ Edition, Gennaro, A. R., Ed., Lippincott, Williams and Wilkins, 2000). These means include, without limitation, the use of enteric coatings, buffers, gels such as hydrogels, excess ligand (such as excess maltol in the case of gallium maltolate), and encapsulation within liposomes. Methods to inhibit or prevent dissociation that are described in U.S. Pat. No. 5,574,027 to Bernstein, which is incorporated herein, are among those contemplated under the present invention.

It is to be understood that the pharmaceutical compositions of the present invention may include one or more active agents in addition to the gallium compositions.

In another embodiment of the invention, there is provided a method of treating a human or veterinary patient for a gallium-responsive disease or disorder through the administration of a therapeutically effective amount of a gallium-containing pharmaceutical composition of the present invention.

Gallium-responsive diseases and disorders contemplated under the present invention include without limitation, cancer, including breast cancer, prostate cancer, liver cancer, cancers of the bone, lymphomas, leukemias, multiple myeloma, cancers of the brain, cancers of the throat, pancreatic cancer, neck cancers, gastric cancers, intestinal cancers, colon cancers, rectal cancers, testicular cancers, bladder cancers, ovarian cancers, cervical cancers, uterine cancers, skin cancers, melanoma, ocular cancers, mouth cancers, tongue cancers, metastatic cancers, and other cancers; conditions of excessive bone resorption and/or disorders of calcium homeostasis, including osteoporosis, Paget's disease, metastatic bone disease, hyperparathyroidism, hypercalcemia, osteonecrosis, laminitis, and navicular disorders; inflammatory and/or autoimmune disorders, including rheumatoid arthritis, inflammatory arthritis, psoriasis and related dermatoses, multiple sclerosis, lupus erythematosus, Sjogren's syndrome, uveitis, asthma, Type 1 diabetes, Graves' disease, autoimmune Addison's disease, Hashimoto's thyroiditis, central nervous system vasculitis, spondylitis, inflammatory bowel disease, Crohn's disease, colitis, celiac disease, myasthenia gravis, inflammatory myopathies, scleroderma, alopecia areata, and septicemia; infectious diseases, including intracellular pathogenic diseases such as tuberculosis, Johne's disease, leprosy, listeriosis, brucellosis, typhoid fever, legionnaire's disease, *Rhodococcus* infections (including those caused by *Rhodococcus equi*), plague, typhus, chlamydia, leishmaniasis, trypanosomiasis, and malaria; *Pseudomonas* infections; biofilm-forming infections; neuropathies including painful peripheral neuropathies; adverse conditions of the liver, including hepatitis, hepatomegaly, and cirrhosis; splenomegaly; and other conditions that are now known, or are discovered in the future, to be responsive to gallium.

When the gallium-containing pharmaceutical compositions are used in such a treatment method, the compositions are administered in a therapeutically effective amount to treat the gallium-responsive disease or disorder. When administered systemically, such effective amounts generally result in maximal plasma gallium concentrations of about 10 to 8,000 ng/mL, preferably about 100 to 3,000 ng/mL, and most preferably about 500 to 1,500 ng/mL. As an example, a liquid pharmaceutical composition comprising 10% w/v gallium maltolate, 30% w/v sucrose, 1% v/v benzyl alcohol, and 0.8% w/v carboxymethylcellulose in de-ionized, sterile water (as described in Example 3) may be administered orally at a gallium maltolate dose of about 0.1 to 100 mg per kilogram body weight per day (0.1 to 100 mg/Kg/day), preferably about 4 to 60 mg/Kg/day, and more preferably about 6 to 40 mg/Kg/day, preferably administered once per day.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents and publications mentioned herein are incorporated by reference in their entireties.

EXPERIMENTAL

The following examples are put forth so as to provide those of ordinary skill in the art with a complete disclosure and description of how to make and use the compositions of the invention. The examples are intended as non-limiting examples of the invention. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

The practice of the present invention will employ, unless otherwise indicated, conventional techniques of pharmaceutical formulation, medicinal chemistry and the like, which are within the skill of the art. Such techniques are explained fully in the literature. Preparation of various types of pharmaceutical formulations are described, for example, in REMINGTON: THE SCIENCE AND PRACTICE OF PHARMACY, 20$^{th}$ edition (Lippincott Williams & Wilkins, 2000) and Ansel et al., PHARMACEUTICAL DOSAGE FORMS AND DRUG DELIVERY SYSTEMS, 6$^{th}$ Ed. (Media, Pa.: Williams & Wilkins, 1995).

EXAMPLE 1

Solid Oral Dosage Forms

The following ingredients in wt % are used to prepare the solid oral dosage forms of the present invention, which includes capsules, tablets, or caplets:
  66.67 wt % Gallium maltolate powder; and
  33.33 wt % Carboxymethylcellulose powder.

For the preparation of a single dosage unit, such as a single tablet, caplet, or capsule, the following amounts of the ingredients are used:
  500 mg Gallium maltolate powder; and
  250 mg Carboxymethylcellulose powder.

A recommended carboxymethylcellulose for use in the formulation of the solid oral dosage forms described herein is AQUALON® sodium carboxymethylcellulose gum, grade 7H3SF, X grind (fine), viscosity of 1% solution approximately 1,000-2,800 cps (Hercules, Inc., Wilmington, Del.).

EXAMPLE 2

Solid Oral Dosage Forms with Sodium Citrate

The following ingredients in wt % are used to prepare sodium citrate-containing solid oral dosage forms of the present invention, which includes capsules, tablets, or caplets:
  62.5 wt % Gallium maltolate powder;
  18.75 wt % Carboxymethylcellulose powder; and
  18.75 wt % Sodium citrate powder.

For the preparation of a single dosage unit, such as a single tablet, caplet, or capsule, the following amounts of the ingredients are used:
  500 mg Gallium maltolate powder;
  150 mg Carboxymethylcellulose powder; and
  150 mg Sodium citrate powder.

A recommended carboxymethylcellulose for use in the formulation of the solid oral dosage forms described herein is AQUALON® sodium carboxymethylcellulose gum, grade 7H3SF, X grind (fine), viscosity of 1% solution approximately 1,000-2,800 cps (Hercules, Inc., Wilmington, Del.).

EXAMPLE 3

Liquid Oral Dosage Forms

The following ingredients in w/v and/or v/v are dissolved and/or suspended in de-ionized sterile water to prepare the liquid oral dosage forms of the present invention:
  10% w/v Gallium maltolate;
  30% w/v Sucrose;
  1% v/v Benzyl alcohol; and
  0.8% w/v Carboxymethylcellulose.

For the preparation of one liter of the liquid oral dosage form of the present invention, the following amounts of the ingredients are used:
  990 mL Water (de-ionized, sterile);
  100 g Gallium maltolate;
  300 g Sucrose;
  10 mL Benzyl alcohol; and
  8 g Carboxymethylcellulose.

A recommended carboxymethylcellulose for use in the formulation of the liquid oral dosage form described herein is AQUALON® sodium carboxymethylcellulose gum, grade 7M2F, X grind (fine), viscosity of 2% solution approximately 150-200 cps (Hercules, Inc., Wilmington, Del.).

At room temperature, add the gallium maltolate to the water with moderately vigorous stirring. Continue stirring for about 30 minutes. With moderate stirring, add the sucrose to the water, allowing it to dissolve completely over a period of a few minutes. With continued stirring, add the benzyl alcohol, and then gradually add the carboxymethylcellulose over a period of several minutes. Continue moderate stirring for 10 minutes.

EXAMPLE 4

Viscous Liquid/Paste Dosage Forms

The following ingredients in w/v and/or v/v were dissolved and/or suspended in de-ionized sterile water to prepare the viscous liquid/paste dosage forms of the present invention:
10% w/v Gallium maltolate;
20% v/v Simple syrup (67 wt % sucrose in water);
1% v/v Benzyl alcohol; and
1.5% w/v Carboxymethylcellulose.

For the preparation of one liter of the viscous liquid/paste dosage form of the present invention, the following amounts of the ingredients were used:
100 grams Gallium maltolate;
200 mL Simple syrup (400 g sucrose in 200 mL water);
10 mL Benzyl alcohol;
15 g Carboxymethylcellulose; and
790 mL Water (de-ionized, sterile).

The carboxymethylcellulose used in the formulation of the viscous liquid/paste dosage form described herein was AQUALON® sodium carboxymethylcellulose gum, grade 7H4F, X grind (fine), viscosity of 1% solution approximately 3,000-6,000 cps (Hercules, Inc., Wilmington, Del.).

At room temperature, gallium maltolate was added to the water with moderately vigorous stirring, which continued for about 30 minutes. With continued stirring, the benzyl alcohol was added to the solution and then the carboxymethylcellulose was gradually added to the solution over a period of several minutes. After about 10 minutes of stirring, the simple syrup was gradually added to the formulation under continued moderate to slow stirring over a period of a few minutes after which the stirring continued for an additional five minutes.

To make the simple syrup, 400 mL of water was brought to a boil and then with continued stirring, 800 g sucrose was added to the boiling water. After the sugar had entirely dissolved, the heat was reduced and the solution was left to simmer for about five minutes with continuous stirring, and water was added with continued stirring to bring the total weight to 1200 g. The solution was then removed from the heat and allowed to cool gradually to room temperature.

EXAMPLE 5

Preparation of Medicated Animal Feed

Animal feed in a form suitable for administration to a particular animal (e.g., hay or other fodder, pellets, chews, kibbles, crumbles, liquids, pastes, etc.) is prepared by adding gallium maltolate to the animal feed in an amount such that the animal receives a daily dose of the gallium maltolate in one day's consumption of feed. For example, for typical horse feed, e.g. hay or prepared pellets, the amount of gallium maltolate to be put into the feed will vary depending on the size of the animal, but will generally be in an amount of about 0.01 to 10 g per Kg of feed, preferably 0.1 to 6 g, and more preferably 1 to 4 g per Kg of feed.

For the preparation of typical horse feed with a concentration of gallium maltolate at 2 g per Kg of feed, the following procedure may be followed: One liter of the liquid composition of Example 3 is added to 50 Kg of solid horse feed (e.g., hay or other fodder, pellets, etc.). The liquid is thoroughly mixed with the solid feed for five minutes, and is allowed to soak into the feed. The feed is then dried in air while spread on a tray, in this case at 40° C. for six hours. The feed is then administered to the horse in a conventional manner. Example of typical horse feed that may be used in the preparation described herein is LMF California Complete horse feed (LMF Feeds Inc., Weiser, Id.)

EXAMPLE 6

Evaluation of Viscous Liquid/Paste Formulation in Foals

A viscous liquid/paste formulation of the invention was investigated for gallium bioavailability in two healthy foals, each foal about six months old and about 175 Kg in weight. For comparison, each foal was first administered gallium maltolate (20 mg/Kg of body weight) in a formulation consisting only of gallium maltolate and water. The formulation was administered intragastrically, via a nasogastric tube. Blood samples were taken from the foals just prior to dosing (0 hours), and at 1, 2, 4, 6, and 8 hours post-dosing, and the serum was separated by coagulation and centrifugation. After a washout period of seven days, the same two foals were each administered the same dose of gallium maltolate (20 mg/Kg of body weight), but this time using the viscous liquid/paste formulation of Example 4, containing carboxymethylcellulose. This viscous liquid/paste formulation was administered by squirting it from a syringe into the back of the mouth, from where it was swallowed. Blood samples were again taken from the foals just prior to dosing (0 hours), and at 1, 2, 4, 6, and 8 hours post-dosing, and the serum was separated by coagulation and centrifugation. Gallium concentrations in all the serum samples were measured by inductively coupled plasma/mass spectrometry (ICP-MS).

The results of the experiment, presented in FIG. 1, show that serum levels of gallium were significantly higher when the oral viscous liquid/paste formulation of Example 4 was administered than when the intragastric aqueous formulation was administered. For foal 1, the maximum serum gallium concentrations ($C_{max}$) were 1.68 µg/mL for the aqueous formulation and 3.03 µg/mL for the viscous liquid/paste formulation (an 80% increase); for foal 2, $C_{max}$ was 1.93 µg/mL for the aqueous formulation and 4.00 µg/mL for the viscous liquid/paste formulation (a 107% increase).

I claim:

1. A method for increasing the oral bioavailability of gallium from an orally administered gallium compound, the increase being relative to the oral bioavailability of gallium from the gallium compound when it is orally administered without a pharmaceutically acceptable viscosity-increasing agent, comprising the administration of a pharmaceutical composition comprising gallium 8-quinolinolate and a pharmaceutically acceptable viscosity-increasing agent to a human or veterinary patient, wherein the viscosity-increasing agent is water-soluble and is selected from the group consisting of methylcellulose, carboxymethylcellulose, hydroxypropyl methylcellulose, other cellulose derivatives and their pharmaceutically acceptable salts, esters, hydrates, and solvates, cellulose, polyethylene glycol, Carbopols, povidones, gum Arabic, and xanthum gum, and wherein the viscosity-increasing agent is not a cross-linked form of carboxymethylcellulose or povidone, and further wherein the composition is a solid state mixture or a viscous liquid/paste.

2. The method of claim 1, comprising a solid state mixture of gallium 8-quinolinolate and the viscosity-increasing agent.

3. The method of claim 2, wherein the weight ratio of gallium 8-quinolinolate to the viscosity-increasing agent is approximately 0.1 to 1000.

4. The method of claim 1, wherein the weight ratio of gallium 8-quinolinolate to the viscosity-increasing agent is approximately 1 to 250.

5. The method of claim 4, wherein the weight ratio of gallium 8-quinolinolate to the viscosity-increasing agent is approximately 10 to 100.

6. The method of claim 1, wherein the viscosity-increasing agent is selected from the group consisting of viscosity-increasing forms of methylcellulose, carboxymethylcellulose, hydroxypropyl methylcellulose, and other cellulose derivatives.

7. The method of claim 6, wherein the viscosity-increasing agent is a viscosity-increasing form of methylcellulose or carboxymethylcellulose.

8. The method of claim 7, wherein the viscosity-increasing agent is a viscosity-increasing form of carboxymethylcellulose.

* * * * *